United States Patent [19]

Holzwarth et al.

[11] 4,409,046
[45] Oct. 11, 1983

[54] METHOD OF AND AN APPARATUS FOR PRODUCING DISPOSABLE SYRINGES AND THE DISPOSABLE SYRINGE PRODUCED

[75] Inventors: Friedrich Holzwarth, Schorndorf; Gerhard Heinze, Weissach, both of Fed. Rep. of Germany

[73] Assignee: SORTIMAT Creuz & Co. GmbH, Winnenden, Fed. Rep. of Germany

[21] Appl. No.: 214,879

[22] Filed: Dec. 10, 1980

[30] Foreign Application Priority Data

Dec. 10, 1979 [DE] Fed. Rep. of Germany ....... 2949553
Dec. 2, 1980 [DE] Fed. Rep. of Germany ....... 3045411
Dec. 2, 1980 [DE] Fed. Rep. of Germany ....... 3045453

[51] Int. Cl.³ .................. A61M 5/34; B29C 19/06; B29C 27/30
[52] U.S. Cl. .................. 156/73.6; 29/469.5; 29/512; 29/523; 156/221; 156/273.9; 156/274.4; 156/288; 156/294; 156/303.1; 156/379.7; 219/483; 604/272
[58] Field of Search ............. 156/293, 294, 350, 363, 156/569, 273.9, 274.4, 379.7, 380.2, 303.1, 288, 221, 73.6, 380.6; 219/61.11, 477, 482, 483; 29/443, 444, 469.5, 507, 512, 523; 128/207.22, 215, 216, 218 N; 604/239, 240, 272

[56] References Cited

U.S. PATENT DOCUMENTS

| 2,980,565 | 4/1961 | Bardach et al. | 156/569 |
| 3,174,890 | 3/1965 | Goyke | 156/272.4 |
| 3,436,803 | 4/1969 | Sarnoff | 29/432.2 |
| 3,437,788 | 4/1969 | Lingley | 219/162 |
| 3,913,421 | 10/1975 | Hawkins | 29/512 X |
| 3,982,097 | 9/1976 | Seider et al. | 219/486 |
| 4,251,310 | 2/1981 | Goldhaber et al. | 156/275 |
| 4,266,543 | 5/1981 | Blum | 128/218 N |

FOREIGN PATENT DOCUMENTS

| 221221 | 5/1962 | Austria . |
| 846769 | 8/1952 | Fed. Rep. of Germany . |
| 1295140 | 5/1969 | Fed. Rep. of Germany . |
| 1491725 | 6/1969 | Fed. Rep. of Germany . |
| 1491743 | 6/1969 | Fed. Rep. of Germany . |
| 1704102 | 6/1971 | Fed. Rep. of Germany . |
| 1357757 | 3/1964 | France . |
| 76751 | 2/1918 | Switzerland . |
| 394500 | 11/1965 | Switzerland . |

Primary Examiner—Michael G. Wityshyn
Attorney, Agent, or Firm—Spencer & Kaye

[57] ABSTRACT

A metallic syringe tube is fused to a plastic fitting into which the tube is inserted so that the inner end of the tube contacts the fitting, by clamping the tube between a counterelectrode which acts as an abutment for the inner end of the tube and a clamping jaw which engages the free end of the tube, and applying a resistance heating voltage to the tube between the counterelectrode and a location between the fitting and the clamping jaw for heating at least a portion of the syringe tube inner end in contact with the fitting to the melting temperature of the plastic forming the fitting.

29 Claims, 20 Drawing Figures

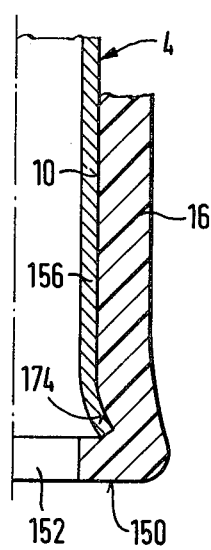
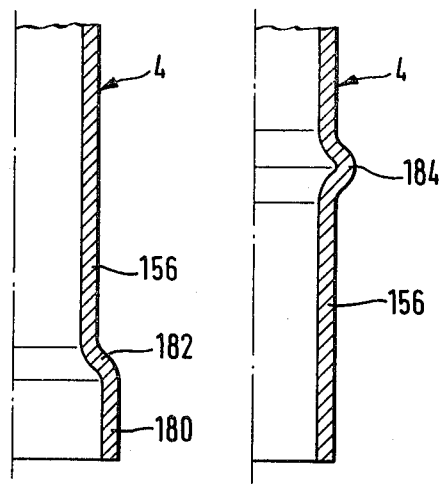
Fig. 7　　Fig. 8a　Fig. 8b
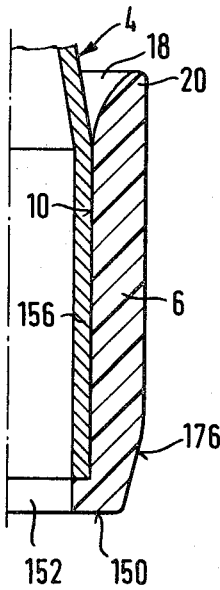
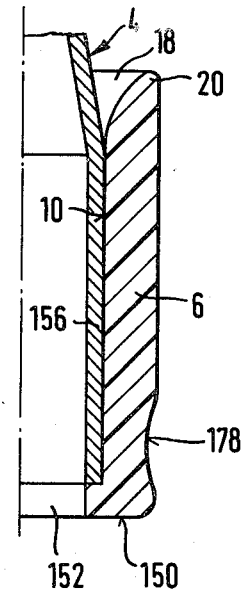
Fig. 9a　　Fig. 9b

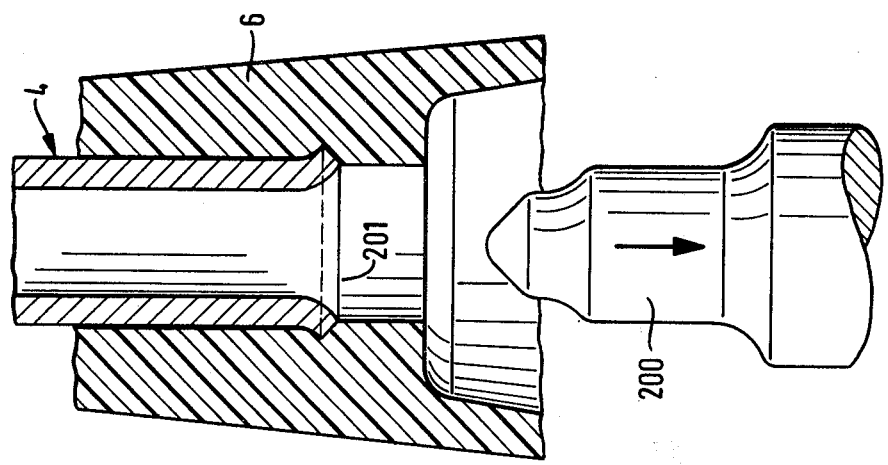
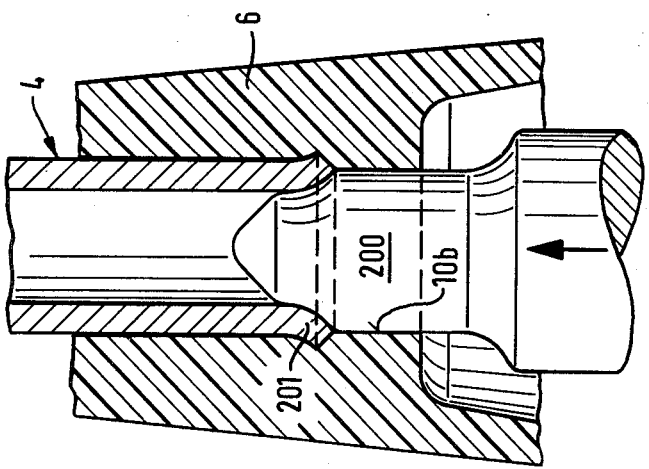
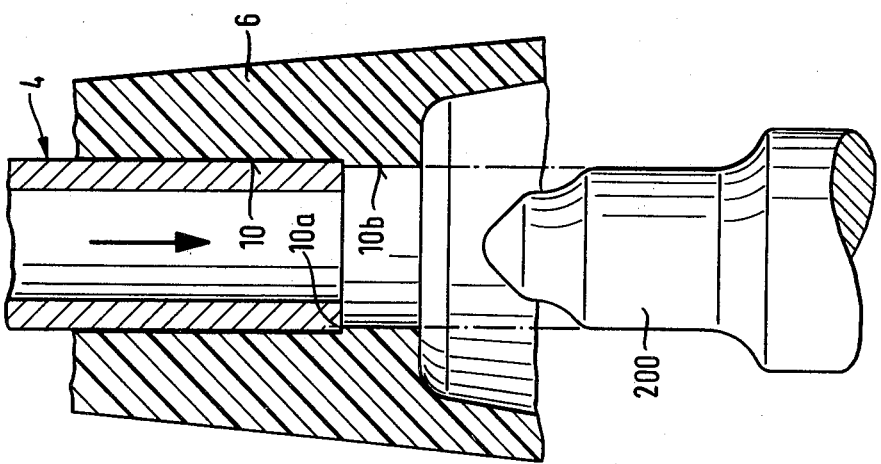

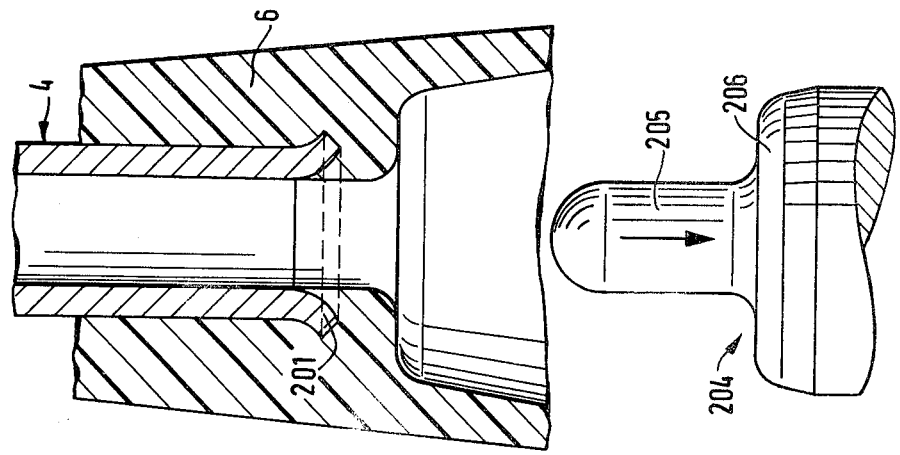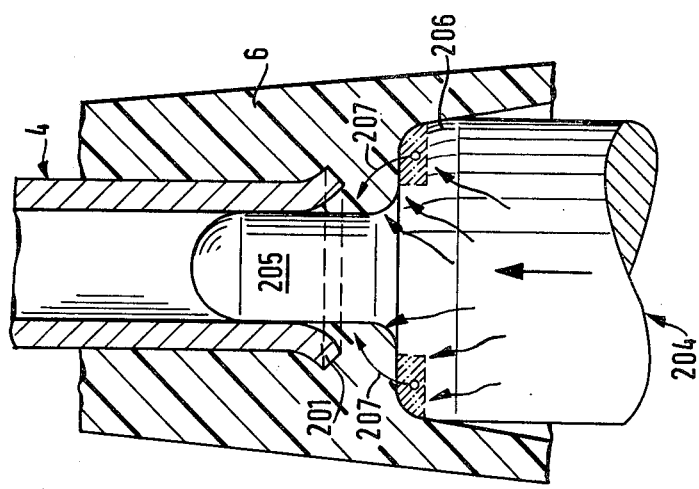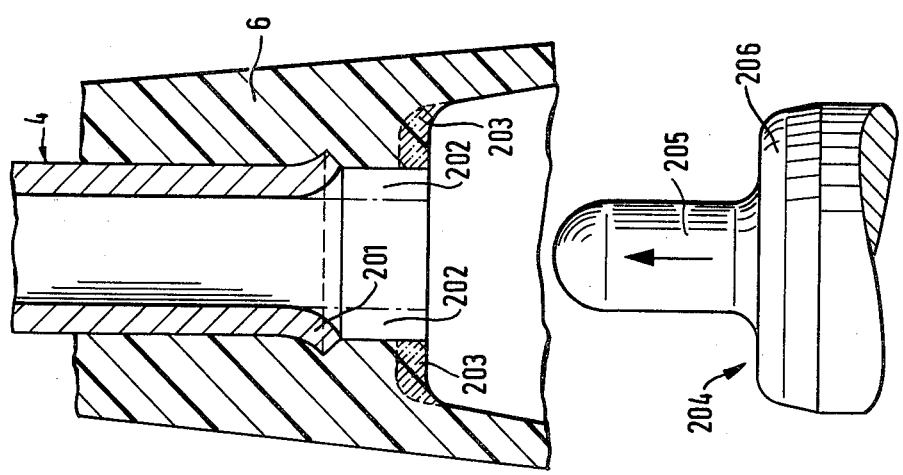

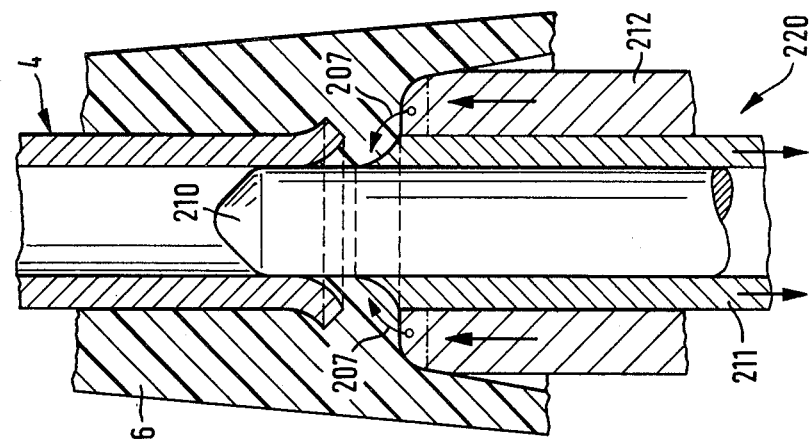
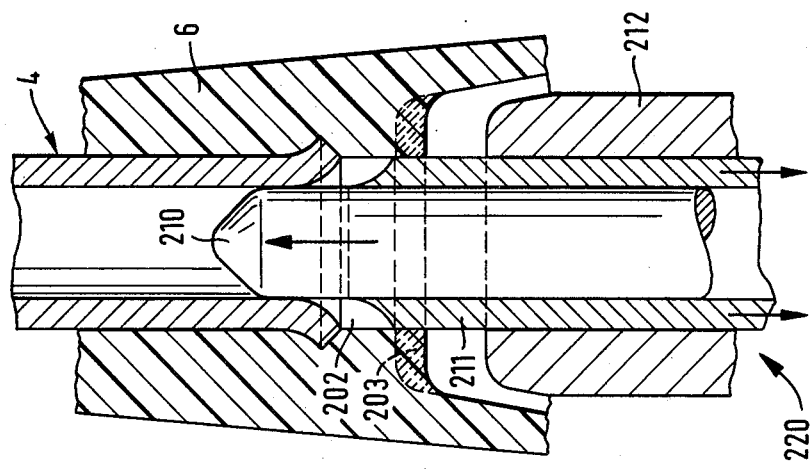
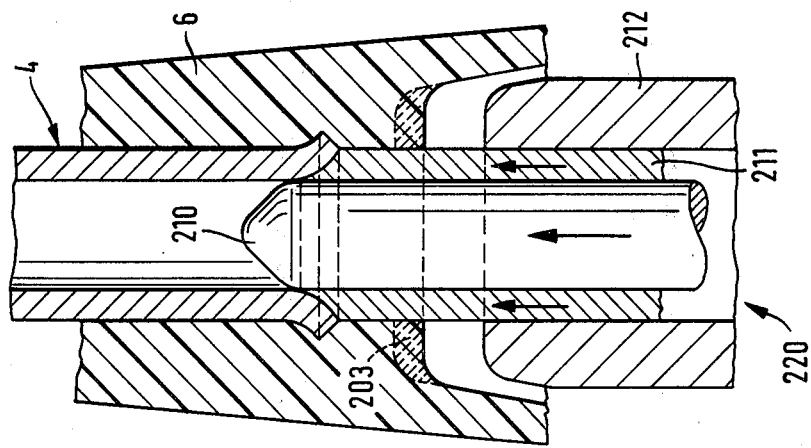

METHOD OF AND AN APPARATUS FOR PRODUCING DISPOSABLE SYRINGES AND THE DISPOSABLE SYRINGE PRODUCED

BACKGROUND OF THE INVENTION

The production of hypodermic needles or syringes, in particular for medical purposes but also for other applications is shifting more and more in the direction of the so-called disposable or one-time syringes which are used only once or but a few times and then discarded. Of course, such hypodermic syringes must function properly, yet on the other hand they must not be complicated or expensive because of their predominant one-time use. It has become customary to use so-called disposable syringes for this purpose. They have a syringe tube, or needle, of metal which is connected in sealing fashion and mechanically firmly with a fitting made of plastic material. The cylinder of the hypodermic syringe containing the piston is then firmly connected with the plastic fitting either by being pushed on or by plastic sealing under the influence of heat. The instant invention is concerned with the production of such disposable syringes consisting of a metallic syringe tube and a plastic fitting.

With all such disposable syringes which include a metal syringe tube and a plastic fitting the tension-proof connection between the syringe tube and the plastic fitting is an indispensable requirement. If the connection is not firm enough, it has happened that the low pressure in a patient's vein propelled the syringe tube with great impulse from the hypodermic syringe into the vein. Then a risky and complicated operation is required, depending on where the syringe tube comes to rest within the human body, leaving aside the fact that also the syringe tube itself, as it is impelled, can cause considerable damage to body organs. On the other hand, leaks can cause loss of the fluid aspired and also present a risk of embolism by air entering into the system. Apart from tensile strength, the syringe tube is to display also pressure strength against being pressed into the fitting.

There are different ways of meeting these demands. The invention relates among other ways to the known one, described in DE-OS No. 17 04 102, of heating the syringe tube by the passage of current to such a degree, for instance, approximately until it is red-hot or to 500° to 600° C. (assumed value, not verified) so that the plastic material of the fitting will fuse together with the syringe tube. In certain analogy with a welding connection, an additional adhesive component may be dispensed with. However, the invention also relates to a mechanical bond of plastic tube and fitting, which bond may be used for pre-fixing the syringe tube in the fitting prior to an adhesion or fusion process on the one hand, or for a general fixation and sealing of the syringe tube in the fitting on the other hand.

Specifically, the invention starts from the applicant's own internal prior knowledge by which the state of the art according to DE-OS No. 17 04 102 was developed further.

With this earlier method the syringe tube first is pushed into the usual receiving bore in the fitting approximately into the position in which the syringe tube is to be connected with the fitting. At the inside of the fitting there is formed a cup facing the main body of the syringe to be mounted later and into which the inner end of the syringe tube projects by a little distance only. It is disputed among experts whether or not this projection by a short distance or a somewhat greater distance is convenient. By no means a great free path length is desired within the fitting so as to avoid the inclusion of air between the inner end of the syringe tube and the wall of the fitting when filling the syringe since this may for example cause the risk of embolism during the later injection of the contents of the syringe into the human body. Thus the space within the fitting before the inner end of the syringe tube is very limited. Therefore a counterelectrode to be applied for resistance heating of the syringe tube was simply placed flush on the free inner end of the syringe tube.

It is also known (DE-OS No. 17 04 102) to have the inner end of the syringe tube end within the central bore of the fitting and to form a central extension on the counterelectrode engaging in the central bore in the fitting and seated on the interior of the syringe tube by a rounded front end face.

On the other hand, the free end of the syringe tube carrying the injection tip outside of the fitting is engaged by a clamping jaw which may be used first to push the syringe tube into the fitting and then to have the syringe tube abut against the counterelectrode in the final position. In the structure previously known to applicant the clamping jaw, at the same time, functions as the second electrode which, together with the counterelectrode, serves to apply welding voltage supplied by a welding voltage generator to the syringe tube for brief resistance heating of the same. Current is pulsed once or several times through the arrangement, depending on the heating technique chosen.

During the passage of the current more or less strong spark erosion takes place between the counterelectrode and the inner end of the syringe tube. Typical erosion lengths are from 0.1 to 0.3 mm. However, under unfavorable conditions the erosion may be much greater, particularly so if welding voltage from the same welding voltage generator is applied during the same process step to a majority or plurality of syringe tubes and the conditions at the individual syringe tubes are not adjusted exactly to the same values. In the case of the above-described arrangement, therefore, the clamping jaw is moved by a predetermined stroke in the direction towards the fixing counterelectrode during the fusion process proper or the passage of the current. The stroke mentioned may be in the order of 1 mm or more, for example, 3 mm. An adaptation to the actual erosion at the inner end of the syringe tube which is clamped between the clamping jaw and the counterelectrode is effected by having a sliding grip between the clamping jaw and the syringe tube in friction lock so that the syringe tube can slip more or less with respect to the clamping jaw during the welding process.

Furthermore, at the side facing the fitting, the clamping jaw is narrowed in funnel shape so that individually supplied syringe tubes can be introduced conveniently into the clamping jaw until the respective syringe tube adopts its proper position in the clamping jaw and the clamping jaw can be closed. This requires a distance of a few millimeters between the exit of the syringe tube from the fitting to the place at which the electrical contact is established between the clamping jaw and the syringe tube. This arrangement provides an inaccurate definition of the place of current transfer between the clamping jaw and the syringe tube, a place which changes during the welding process, and, finally, a relatively great distance between the place of entry of the syringe tube into the fitting and the place of the actual current transfer between the clamping jaw and the syringe tube outside of the fitting. This may cause irregularities in the conditions of fusing because of an insufficiently defined resistance path. Furthermore, with some metals of the syringe tube this may cause optically undesirable annealing colors on the free end of the syringe tube outside of the fitting because of an annealing of the syringe tube which did not become effective for the fusion process. Finally, it may also make the metal of the syringe tube undesirably brittle.

SUMMARY OF THE INVENTION

It is the object of the present invention to improve the conditions of fusion and consequently the quality of the disposable syringes made, at the same time, specifically achieving an adaptation to the operating conditions of multiple manufacture.

This object is met by a method in accordance with the invention of producing disposable syringes, including fusing a metallic syringe tube into a plastic fitting by pushing the syringe tube into the fitting, clamping the syringe tube between a counterelectrode which acts as abutment for the inner end of the syringe tube and a clamping jaw which engages the free end of the syringe tube, and temporarily applying a resistance heating voltage between the counterelectrode and the free end of the syringe tube projecting from the fitting, while, at the same time, displacing the clamping jaw and the counterelectrode relatively towards each other, in that the resistance heating voltage is applied to the free end of the syringe tube between the fitting and the clamping jaw. The fact that at the free end of the syringe tube the welding voltage is no longer applied in the clamping jaw but instead at a place between the fitting and the clamping jaw makes it possible to uncouple the design and kinematics of the mechanically effective parts of the clamping jaw from the desired conditions of current transfer at the free end of the syringe tube and thus obtain the optimum of electrical transfer conditions. For example, the clamping jaw need no longer be electrically conductive as an electrode, but instead may be designed solely with a view to its clamping function and, if desired, its moving function. A feed hopper, for instance, for individually supplied syringe tubes may still be provided at the clamping jaw at the side facing the fitting without increasing the effective resistance length of the syringe tube outside of the fitting. Rather, the feeding of current into the free end of the syringe tube now may be effected directly where or near the place where it has its exit from the fitting. Unnecessary annealing of the free end of the syringe tube outside of the fitting thus is avoided as well as any accompanying annealing colors which have reached lengths of as much as 3 to 5 mm when applying the known process, unless a special metal was used which does not become tarnished even by annealing. The syringe can no longer become brittle or soften in this area whereby safety is increased against any bending or even breaking off of the free end of the syringe tube, perhaps even the inclusion of a broken off syringe tube tip in a vein is avoided. Finally, the transfer resistance between the electrode engaging the free end of the syringe tube and the syringe itself can be kept low and uniform, while optimum pairing of contact materials is permitted regardless of the mechanical clamping conditions.

The invention offers advantages even if the syringe tube is not moved within the fitting by means of the clamping jaw in the direction towards the counterelectrode during the welding process, but instead the counterelectrode is adjusted for compensation of the erosion loss between the counterelectrode and the inner end of the syringe tube, e.g. by causing it to follow the eroding inner end of the syringe tube under spring force or another adjusting force. In that event, in general, the clamping jaw and the point of application of the welding voltage at the free end of the syringe tube will be selected to be stationary. Yet such advantages as being able to separately design the current transfer and the mechanical mounting with respect to the selection of the material thereof as well as the mechanical forces applied are maintained.

These advantages become even more distinct if relative displacement is permitted between the clamping jaw and/or the electrode applied to the free end of the syringe tube. This may be effected either, as known, by providing a given working stroke of the clamping jaw and thus also a stroke of the syringe tube moving towards the counterelectrode which, in general, will be stationary in that case. And it may also be realized in that the counterelectrode as well as the clamping jaw are supported resiliently in mutual harmony.

In this case the current transfer may be effected by much smaller forces and, in the extreme case, with a stationary arrangement of the current transfer. For example, the current transfer may be accomplished by contact brushes which would be entirely unsuitable for mechanically holding the syringe tube.

In fact, it is usually preferred to arrange the counterelectrode to be stationary so as to guarantee that the inner end of the syringe tube will always project by exactly the same predetermined distance within the cup-shaped cavity of the fitting or the corresponding inner area of the fitting in case of a different embodiment. If, under these conditions, the clamping jaw is displaced towards the fitting during application of the resistance heating voltage in the manner described, as known, preferably the resistance heating voltage is applied to the free end of the syringe tube at an unvarying spacing from the fitting. In spite of the adjusting movement of the syringe tube for compensation of the spark erosion at the inner end of the syringe tube, a constant resistance length is maintained during the entire welding time between the electrode applied to the free end of the syringe tube and the counterelectrode in the syringe tube. This provides for much more uniform fusing conditions as compared with the method realized earlier. This is particularly true also if the same welding voltage is used during one operating step to fuse several or even a great number, such as ten syringe tubes at the same time in their respective fitting.

With the earlier method the individually supplied syringes were first thrown against a baffle face for reception in the clamping jaw. During that procedure the syringes sometimes jumped back more or less from the baffle plate before they were finally gripped by the clamping jaw. To balance that, the stroke of the clamping jaw in the direction towards the counterelectrode for compensation of the erosion had to be relatively long. The invention is promoted still further if the syringe tube is fixed in its starting position in the clamping jaw by an auxiliary force before the working stroke of the clamping jaw required during the fusion takes place. If a baffle face is used, as mentioned above, preferably the syringe tube is held in abutment against the baffle face by a return force until the clamping jaw grips the same.

Instead of feeding the syringe tube into the clamping jaw like a projectile, an alternative may provide for controlled feeding such that the syringe tube is placed in engagement with a counter-face aligning the syringe tube in the open clamping jaw by an entrainment force or that the syringe tube is held in another defined end position until gripped by the clamping jaw. If the syringes are made of permanent magnetic material or at least of magnetizable material, which are usually not used in practical application, such an entrainment force could be applied by a guide magnet which might for example be a permanent magnet. If the material of the syringe were magnetizable it would also be possible to have electrodynamic guide forces act from the outside. It is also conceivable to generate eddy currents within the syringe tube and to guide this condition electromagnetically from the outside. Also a mechanical or fluid-mechanical connection between the guide force and the syringe tube during the feeding is conceivable. It was already mentioned that the method according to the invention has increased significance if several or even a great number of disposable syringes are produced and subjected to a common resistance heating voltage during that process. Such a simultaneous multiple production has been realized before.

Great variations occur in the overall effective resistance for resistance heating of the syringe tubes if at least one of the syringe tubes does not reach its operative position for the fusing. In that case, in general, the welding voltage for the other syringe tubes is overdosed, and overheating occurs with all its disadvantageous consequences regarding the quality of the product.

This may be overcome according to a further refinement of the invention depicted in FIG. 4. This refinement of the invention is to be seen in the fact that the at least relatively constant state of the effective heating resistance aimed at by the invention becomes invalid if great disturbances of the operating conditions, in particular of the effective heating power occur from other sources. The measures illustrated in FIG. 4, however, can be used advantageously also with the known. The same applies to the structure of FIGS. 1 and 3 which provides a measure for positively acting against the failure of a syringe tube at its mounting place.

It has already been suggested to dispose the syringe tubes in a magazine and have them withdrawn singly by a separating slide means in the direction towards the respective clamping jaw. Yet it may happen that the syringe tube becomes jammed in the separating slide means or does not become free from the same for other reasons. To counteract such blocking of the supply of syringe tubes, preferably, a withdrawal force acting in friction lock on the syringe tube disposed in the separating slide means is applied for positively ejecting the syringe tube.

Fundamentally, welding or sealing of the thermoplastic material of the fitting and the syringe tube can be obtained already by a sufficiently tight loose insertion of the syringe tube in the central bore of the fitting. However, the quality of the bond can be improved and the production cycle times reduced if the syringe tube is expanded into tight abutment against the fitting prior to the welding process. The engagement may be by friction lock or, preferably, by form lock. Although it may be sufficient in special cases to have a mechanical connection between the syringe tube and the fitting which is only tension-proof or only pressure-resistant, a resistance against tensile as well as compressive forces is preferred. A tension resistance of more than 3 kp, and preferably more than 8 kp, is preferred.

If the syringe tube is expanded mechanically into the fitting, in principle, it is even possible to avoid subsequent resistance welding altogether since the tensile strength which may be obtained, for example, can amount to 8 kp and even considerably more. Even good sealing can be obtained by corresponding expansion in all radial directions. The tensile strength required depends on the syringe diameter. A tensile strength of 8 kp will be sufficient in case of thin syringes (e.g. 0.5–0.8 mm outer diameter). In case of thicker syringes, and values obtained for tensile strength range between 10 and 20 kp or more.

The syringe tube may be expanded into a preformed recess in the fitting. In that event hardly any or no material of the fitting need be displaced. However, it is also possible to work with material displacement alone.

In many cases material displaced by expanding the syringe tube will cause deformation of the lateral outline of the fitting. This can be avoided by the measure depicted in FIGS. 9a and 9b. Thus a recess is to be formed in the pre-shaped configuration of the fitting where material will be displaced upon expanding the syringe tube.

Tensile strength and compressive strength can be achieved by an engagement in friction lock alone between the expanded syringe tube and a central bore of the fitting. To this end, in the extreme case, the central bore may have a constant cross section over the full length of the engagement section of the syringe tube in the fitting. Preferably, however, a constriction of the central bore is provided before the inner end of the syringe tube, as shown in FIGS. 6 and 7. In the state prior to assembly, this constriction may serve for loosely supporting the syringe tube, whereas after expanding the syringe tube it can be drawn upon for supporting the inner end of the syringe tube, thus warranting the pressure resistance of the syringe tube in the fitting. If the syringe tube has a somewhat smaller inner cross sectional area than the constriction before being expanded, the dimensioning may be such that the mandrel just fits through the inner opening of the constriction in the central bore provided in the fitting and expands the inner tube to such an extent that the inner width of the syringe tube becomes equal to the inner width of the constriction. Yet the expansion may be carried on beyond that to a certain degree, taking into consideration that the portion of the constriction which took part in the expansion will spring back elastically to a greater or smaller extent after the expanding work done on the syringe tube.

It is advantageous not only with this arrangement including the constriction, but in general, if the inner end of the syringe tube does not project by a certain extent inwardly towards the hypodermic syringe from the base of the fitting surrounding the syringe tube. In that manner the formation of dead space between a projecting end of the syringe tube and the wall surface of the fitting can be prevented positively at the place where the syringe tube opens into the space of the hypodermic syringe in the connection zone between the fitting and the cylinder of the hypodermic syringe. Although it is known per se to place the counterelectrode flush on the inner end of the syringe tube within a central bore formed in the fitting as described in DE-OS 17 04 102, the invention provides the further possibility of placing the counterelectrode in abutment against the inner face of the syringe tube and thus adjust the place of contact exactly, regardless of the position of the inner end of the syringe tube. If desired, it is even possible to use the mandrel by which the syringe tube is expanded also as the counterelectrode.

Whether an expansion of the syringe tube into form lock is provided for the pre-fixing of the syringe tube in the fitting or for the exclusive connection of the same with subsequent fusing of the thermoplastic material of the fitting on the syringe tube, in both cases FIGS. 5–18 illustrate novel embodiments of a syringe tube made of metal, having a fitting made of thermoplastic material, which syringe tube can be produced by the method of the invention. In exceptional cases the two-sided locking of the syringe tube in the fitting under form lock may also be replaced by one-sided fixing only against tensile or compressive forces or by friction-lock engagement. The tensile strength and pressure resistance required were already explained above in the description of the method according to the invention.

The invention also relates to an apparatus for producing disposable syringes, including metallic syringe tubes and plastic fittings, comprising a holding means for the fitting, a counterelectrode adapted to be engaged with the inner end of the syringe tube, a welding voltage generator, and a clamping jaw gripping the free end of the syringe tube and disposed at an adjustable spacing with respect to the counterelectrode, as already explained above in connection with the method defined in the preamble of the claim. The apparatus according to the invention may be used for carrying out the method according to the invention and includes preferred structural means for realizing the individual method steps.

FIGS. 1 and 2 illustrate an electrode tongs which becomes effective at a certain place in order to permit an application of the resistance heating voltage to the free end of the syringe tube between the fitting and the clamping jaw. This has advantages as compared with the possible contact brush arrangement mentioned above in that the tongs can be closed and released readily, as required. Furthermore, together with the mechanical closing elements it may serve as an electrode, if necessary or, as an alternative, it may be designed to be so stable that its contact face area permits separate current supply. Finally, it also guarantees that closing pressure can be effected at least on two sides and, if required, also the voltage can be applied at least at two sides. Preferably, at least one jaw of of the electrode tongs, preferably both jaws have a contact area approximately in the shape of a dot or line. The contact surface may be constituted by contact material which is adapted to the material of the syringe tube so as to form a contact pair, and the respective closing jaw of the electrode tongs is coated with this contact material, preferably in exchangeable manner.

If the clamping jaw is displaceable under friction lock with respect to the syringe tube in a direction towards the receiving place of the fitting in its holding means so as to compensate the erosion of the inner end of the syringe tube when applying welding voltage, preferably the electrode tongs is arranged to be stationary in close proximity to the exit of the syringe tube from the plastic fitting and under lighter friction lock than the clamping jaw with respect to the syringe tube. In general the electrode tongs is supported to be freely floating in order to avoid canting. This does not lead to any inconvenient interaction with advancing movements of the main jaw nor to disturbances during the closing and opening motions of the electrode tongs. Conveniently, the latter is spring-biased in its closing position and provided with an opening cam control means.

If, furthermore, a glide path is provided for feeding syringe tubes singled out, for example in the form of a glide rail effective by gravity or a pneumatic supply hose, which glide path ends at a baffle face behind the open clamping jaw, it is convenient to provide a friction roller which takes along the respective syringe tube towards the baffle face and prevents the syringe tube from hitting the baffle wall and bouncing back into an undefined final position. Conveniently, the friction roller is supported to be stationary between the clamping jaw in its receiving position and the baffle face or, as an alternative, in the clamping jaw.

FIG. 4 illustrates a preferred apparatus for detecting the number of syringe tubes ready for fusing and for corresponding adjustment of the respective welding capacity required. In this context it is taken into consideration that even in the absence of a fitting, at best, scrap to be sorted out later is produced by unnecessary annealing of the respective syringe tube, whereas the quality of the operating conditions regarding the remainder of the pairs of syringe tubes and fittings is not imparied by the blank annealing of any such syringe tube.

According to an advantageous feature a preferred embodiment of the detecting means shown in Fig. 4 syringe tubes present are detected by using parallel resistance measuring sections which pass through partial sections of the syringe tubes. As an alternative, a different kind of detector could be used, such as photoelectric detectors, just to mention one of a great variety of detectors available to those skilled in the art.

Finally, FIGS. 1 and 3 show a preferred structure solution for applying a withdrawal force in friction lock on syringe tubes lying in the separating slide means in order to be sure that when using a syringe tube magazine with a slide means to single out syringe tubes the latter are positively ejected from the separating slide means so that the feeding of syringe tubes is as uninterrupted and uniform as possible. For this purpose a friction roller is supported in the separating slide means. The friction roller is preferably supported and designed so that it does not obstruct the reception of the respective syringe tube in the separating slide means and, in addition to the centrifuging effect in friction lock, serves as an ejector of the syringe tube from the separating slide means when in discharge position.

The disposable syringes produced in accordance with the method or the apparatus of the invention display an extremely high uniform strength between the syringe tube and the fitting, even when produced in series. They can be so produced that perfect sealing is warranted. They are greatly improved as regards the softening or becoming brittle of the material. Furthermore, they permit a constant exact positioning of the syringe tube in the fitting and they can be used with a great variety of pairings of material between the fitting and the syringe tube. Finally, they are also optically pleasant as annealing colors at the free end of the syringe tube practically do not occur or are greatly reduced. To give better contact, corresponding precious materials can be utilized purposefully and, therefore, in cost-saving manner. And in spite of apparent greater expenditure, savings may even be made, if desired, by designing the clamping jaw with a view to its clamping and moving functions. Plastic materials which have no tendency to absorb water may be used in preparing the fittings.

The invention further may be used with a plurality of materials and geometric shapes of the fittings as well as materials and configurations of the syringe tubes as offered quite differently by different manufacturers. Preferred fittings are made of polyamide 6 or polyamide 66 and/or preferred syringe tubes are made of steel, grade V2A or V4A.

At constant sliding stroke with respect to the syringe tube the clamping jaws can be made of a material which has good sliding qualities and is resistant against abrasion at least in the clamping area so that also the sliding grooves otherwise formed can be reduced. Brass may be used as the contact material of the tongs, e.g. if the entire tongs are made of brass. It is also possible to use silver, preferably as coating for the tongs. Quite generally, the contact area of the electrode cooperating with the free end of the syringe tube may be made of a material which pairs well, such as silver or tungsten. Conveniently, tungsten pins are used as counterelectrodes, as is already known. The counterelectrode may either be placed flush on the inner end of the syringe tube, or it may be given a certain geometric course suitable for the electrical contact transition, e.g. the configuration of a cone which is drawnin in funnel-shape at the counterelectrode.

Furthermore, the invention also relates to specially designed disposable syringes and to a method of and an apparatus for producing such syringes. These syringes may be provided with a solely mechanical sealing connection between syringe tube and fitting, possibly in combination with an additional adhesive bond. However, this mode of connection may also serve for preparing the fusion of the syringe tube in the fitting. Various possibilities are elucidated in more detail at the end of the specification (FIGS. 8 to 18) by way of example.

BRIEF DESCRIPTION OF THE DRAWING

The invention will be described further, by way of example, with reference to the accompanying drawings, in which:

FIG. 7 is an axial cross-sectional detail view of an expanded form of syringe tube and fitting to be obtained by the arrangement according to FIG. 6;

FIGS. 8a and 8b are longitudinal cross-sectional detail views alternative embodiments of a wall of expanded syringe tubes;

FIGS. 9a and 9b are cross-sectional detail view of two alternative embodiments of the fitting, the outer end of which is pre-shaped in different manners, each figure showing in addition a cylindrically expanded end of the syringe tube;

FIGS. 10 to 15 are longitudinal cross-sectional views of the fitting and the syringe tube in respect of a first manner of expanding the syringe tube with subsequent formation of plastic material of the syringe tube in front of the inner end of the syringe tube in different procedural phases;

FIGS. 16 to 18 are views similar to those of FIGS. 10–15 of an alternative to the above-mentioned embodiment, again in different procedural phases.

DESCRIPTION OF THE PREFERRED EMBODIMENTS

Figure 1:
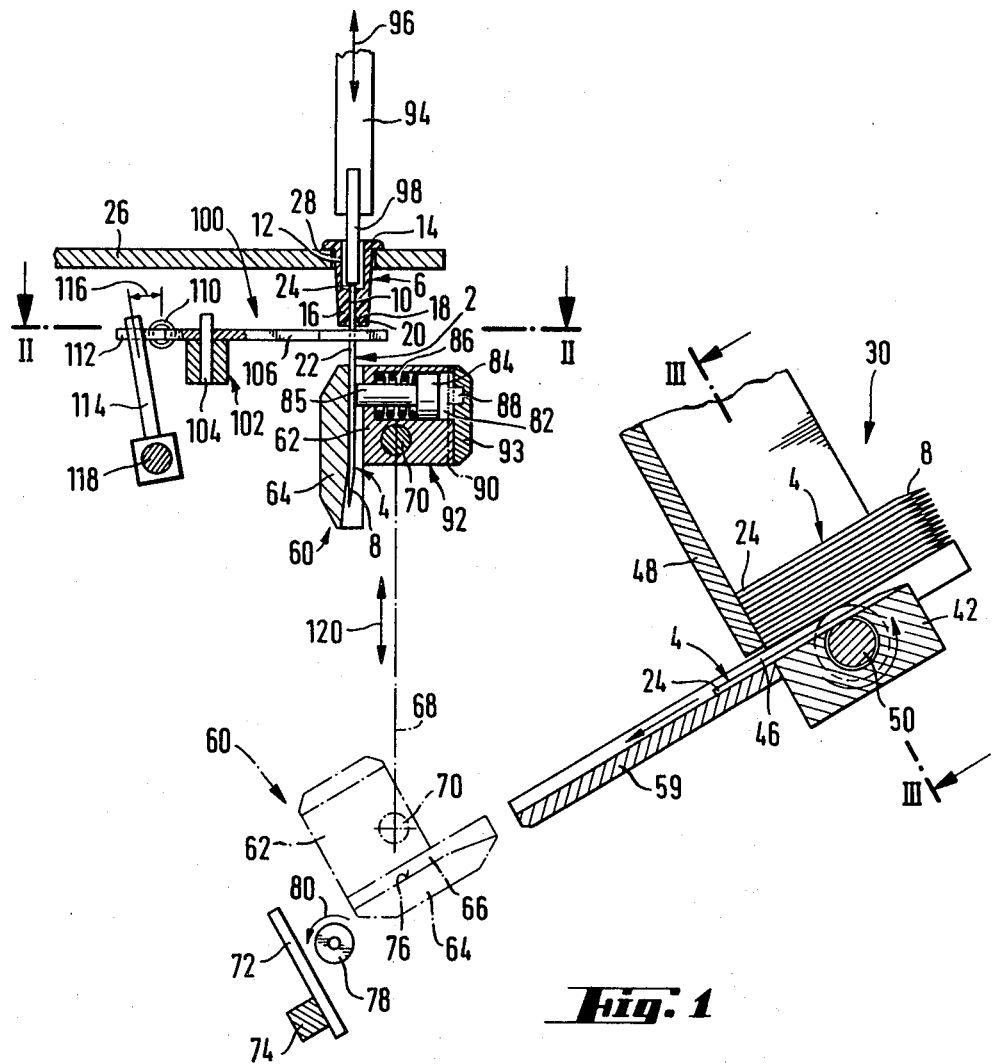
FIG. 1 is an elevational, cross-sectional view of essential parts of an apparatus according to the invention.

FIG. 1 shows one of a great variety of practicable embodiments of a disposable syringe 2 in position for fusing its metal syringe tube 4 into a fitting 6 made of thermoplastic material. The syringe tube 4 is a thin tube or hollow needle having an injection tip 8 at its outer free end. The syringe tube 4 enters through a central bore 10 in the fitting 6 into the interior thereof which is defined by a cup-shaped portion 12 of the fitting. A flange-like enlargement 14 is formed at the free end of the fitting for connection to the body of the hypodermic syringe proper. The central bore 10 of the fitting 6 is formed in the base 16 thereof from which the cup-shaped portion 12 starts. The base 16 is constricted somewhat at 18 where the free end of the syringe tube 4 leaves the fitting 6 so that an annular collar 20 facing the free end 22 of the syringe tube defines the exit of the free end 22 from the fitting 6. The inner end 24 projects a little, by a predetermined distance, beyond the base 16 within the interior of the fitting 6 defined by the cup-shaped portion 12 of the fitting 6. The free end 22 of the syringe tube 4 has a greater length than the fitting 6. Moreover, the length of the interior space defined by the cup-shaped portion 12 of the fitting 6 is much greater than the length of the inner end of the syringe tube. This interior space in the fitting 6 may be centrosymmetrical with respect to the syringe tube.

Apart from the embodiment described of a disposable syringe 2 there is a great variety of other embodiments to which the invention is applicable analogously.

The central bore 10 in the fitting 6 is so dimensioned that it tightly surrounds the syringe tube 4 so that upon heating of the syringe tube 4 the surrounding material of the wall of the base 16 is fused on to the syringe tube.

The fusing apparatus comprises a carrier plate 26 in which a receiving aperture 28 is formed for a plurality, e.g. two or preferably more, e.g. five or ten fittings 6 which can be suspended in the receiving aperture 28 by supporting their flange-like enlargement 14 on the carrier plate 26.

The other receiving places are to be imagined in continuation behind the receiving aperture 28 shown in a direction normal to the plane of the drawing. Although FIG. 1 shows only one apparatus for fusing a single syringe tube 4 in its fitting 6, a corresponding multiplication also of the other elements of FIG. 1 must be conceived normal to the plane of the drawing.

Figure 3:
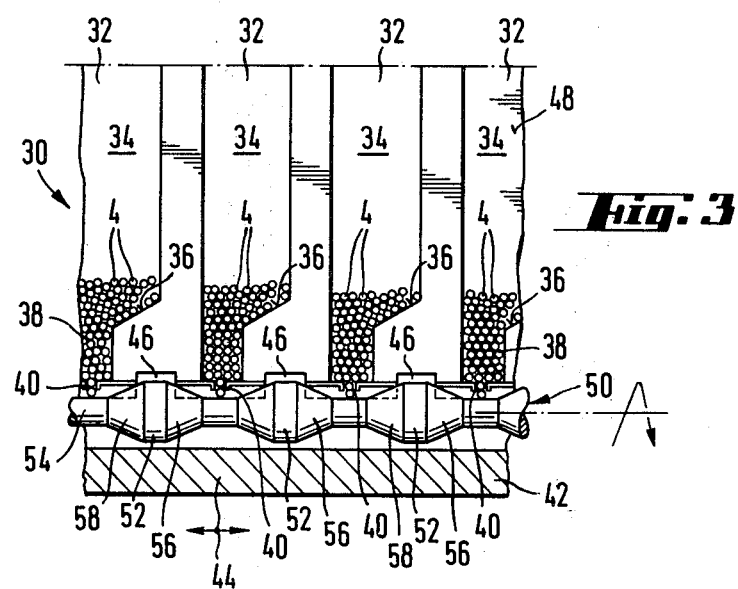
FIG. 3 is an elevational view, partly in cross-section along the line III–III of FIG. 1 and partly diagrammatic, of a magazine means for syringe tubes according to FIG. 1.

First, the syringe tubes 4 are made available in a syringe tube magazine 30 (cf. also FIG. 3). A separate storage space 32 for syringe tubes 4 is associated with each working station of the multiple arrangement. Each storage space 32 has a larger storage volume 34 proper which narrows into a lower feed chamber 38 by an at least one-sided oblique wall 36. At the bottom of the feed chamber receiving chambers 40 for individual syringe tubes are formed in a separating slide means 42 adapted to reciprocate in the direction of the double arrow 44 by the extent shown in FIG. 3. The back and forth movement of the separating slide means is so dimensioned that one syringe tube 4 each in the receiving chamber 40 of the separating slide means can be conveyed to a position below the entry 46 of a glide channel leading further on. The arrangement is such that the individual syringe tubes 4 are transported in the glide channel with their inner ends leading. This can be seen particularly clearly in FIG. 1 in which the tips 8 of the individual syringe tubes 4 are shown remote from glide channel 46 serving as entry. As shown in the drawing, the respective syringe tube magazine 30 is positioned at such an inclination that the inner ends 24 of the syringe tube 4 at first are supported and aligned along a rectilinear supporting wall 48.

A first friction roller 50 is supported for rotation about its axis in the separating slide means 42. It is rotatable at least during the procedure of withdrawal of a syringe tube from the syringe tube magazine 30 (in the direction of the arcuate arrow shown in FIG. 1.

The friction roller 50 further has sections 52 each of constant diameter and section 54 which is axially longer, and have a constant smaller diameter than sections 52.

The sections 52 and 54 alternate and are interconnected symmetrically with respect to each other by conical transitory sections 56 and 58 of decreasing and increasing diameters, respectively.

In addition, the first friction roller 50 is displaceable axially along the path of the stroke of the separating slide means.

The arrangement is such that upon reception of a syringe tube 4 in the corresponding receiving chamber 40 of the separating slide means 42 the bottom of the receiving chamber 40 is formed by the section 54 of smaller diameter of the friction roller. In this position the syringe tube 4 can be taken up completely in the separating slide means and be conveyed by the same towards the entry 46 of the continuing glide channel 59. The transfer from the receiving chamber 40 into the entry 46 is enhanced not only because the friction roller rotates or is set into motion but also by an additional ejection movement of the syringe tube 4 from the receiving chamber 40 into the entry 46 by virtue of additional axial displacement of the first friction roller 50 with respect to the separating slide means. This has the effect that first one or the other of the conical transitory sections 56 or 58 limits the depth of the receiving chamber 40, depending on the direction of the axial displacement, until finally in the extreme case—not always required—the section 52 with the greater diameter has reduced essentially or entirely the receiving depth of the receiving chamber 40. During the return stroke of the separating slide means the procedure described is reversed until the starting position described is reached.

As shown in FIG. 1, a glide rail 59 which forms the continuation of the entry 46 is inclined downwardly so that the individual syringe tubes 4 are conveyed by gravity alone, maintaining their position as determined in the magazine. The glide rail 59 may also be replaced by an inclined pipe or hose conveyor or, if desired, also by a fluid conveyer, in particular a pneumatic conveying means. For example, the glide channel may be closed in tubular shape and the entry 46 subjected to pressurized air.

A clamping jaw 60 is aligned with the glide rail 59 and disposed such that the syringe tube 4 arriving on the glide rail 59 enters into a receiving channel 66 between two jaw members 62 and 64. As shown in FIG. 1, the lower jaw member 64 is extended in the direction towards the glide rail and slightly chamfered towards the outside or bent at the bottom of the receiving channel 66 to guarantee smooth entry of the syringe tube arriving in the receiving channel. A corresponding funnel-like curvature may also be provided at the shorter jaw member 62.

The clamping jaw 60 is shown in alignment with the glide rail 59 by chain lines, this being its lower inclined position. It may be lifted, and pivoted at the same time into an upper position shown by solid lines and in section in FIG. 1. The length of the stroke is indicated by the dash-dot line 68. Pivoting is effected by pivot pins or a pivot shaft 70.

In the lower position, shown in chain lines, the receiving channel 66 of the clamping jaw 60 at first is open so that the syringe tube gliding down can fall freely with its inner end through the receiving channel 66 and impinge against the baffle face of a stationary baffle plate 72 carried by a mounting beam 74. Between the baffle plate 72 and a glide path 76 in the lower jaw member 64, in other words at the bottom of the receiving channel 66, a second friction roller 78 is supported stationarily in the path of the arriving syringe tube 44 and so as to be rotated in the direction of the arrow 80 so that it moves a syringe tube which may bounce back from the baffle plate, into abutment against the baffle plate 72, and keeps it there.

A pneumatic cylinder 82 guiding a piston 84 is formed in the upper jaw member 62. The piston carries a smaller piston rod 85 the free end of which, together with the upper jaw member 64, defines a clamping jaw for gripping the syringe tube 4 aligned along the baffle face within the receiving channel 66.

A piston spring 86 normally biases the piston in outward direction so that the receiving channel 66 remains free. It is moved into the upper closing position, shown in solid lines in FIG. 1, by being subjected to pressurized air through a supply channel 88 leading towards the outer end face of the piston 84.

In the case of a multiple arrangement, a common actuating diaphragm 90 for the individual pistons 84 disposed side by side in individual cylinders can be clamped between the body 92 of the upper jaw member and a common cylinder cover 93 in which the supply channel 88 is formed, as roughly indicated by an additional chain line in the upper part of FIG. 1.

In that case a single common upper jaw member 62 and a single common lower jaw member 64 each can be provided for the various units of pistons and cylinders 82 and 84, respectively. The terms "upper" and "lower" relate to the lower position of the clamping jaw 60 shown in chain lines in FIG. 1.

As soon as the syringe tube received in the respective receiving channel 66 has been aligned on the common baffle plate 72, the piston rod 85 can be pressed against the syringe tube 4 which is supported on the jaw member 64 so that the syringe tube will be clamped ready for transportation in the clamping jaw. Then the clamping jaw is moved into the upper position shown in solid lines in FIG. 1. During this procedure the syringe tube 4 is aligned with the central bore 10 in the fitting 6 and also pushed in a lifting procedure by its inner end 24 into the end position in the fitting 6 shown at the top of FIG. 1.

Above the receiving aperture 28 in the carrier plate 26 a rod-shaped current conductor 94 is movable up and down as shown by double arrow 96. The current conductor 94 carries a counterelectrode 98 made of tungsten which is placed flush on the inner end 24 of the syringe tube or in another suitable defined position which provides little transfer resistance, at the same time, largely filling the small interior of the fitting 6 within the cup-shaped portion 12. The syringe tube 4 is clamped between the counterelectrode 98 and the clamping jaw 60.

Figure 2:
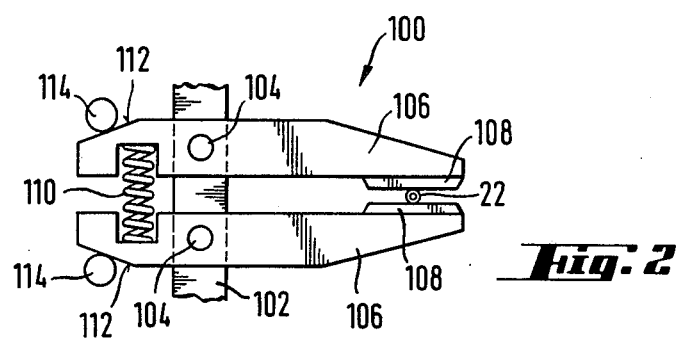
FIG. 2 is a top plan view of the electrode tongs of the apparatus of FIG. 1.

An electrode tongs 100 shown in greater detail in FIG. 2 constitutes the other electrode which cooperates with the counterelectrode 98 and by means of which welding voltage can be applied to the section of the syringe tube 4 disposed between the two electrodes so as to heat the same until the neighboring plastic material in the fitting is fused on to the syringe tube. To this end both electrodes can be connected to a welding voltage generator which operates with relatively low voltage values in the range of a few volts but with relatively high current values in the order of several amperes.

It is convenient to provide a voltage stabilizing means (not shown) so as to guarantee the operating conditions at each welding location even during simultaneous welding at a plurality of locations. If the resistivities and geometric conditions vary a lot, an alternative or additional measure can be taken to regulate the welding current so that it will adopt a rated value in the respective resistance welding path.

The electrode tongs is held stationary in a freely floating manner on two bearing pins 104 in a bearing 102 which is resilient in every direction so that the electrode tongs 100 is aligned horizontally and pivotal about the two bearing pins 104 by both its tongs halves 106. Two contact coatings 108, which are preferably exchangeable, are disposed opposite each other in the head of the tongs to grip the free end 22 of the syringe tube 4 between them. The configuration of the contact may be of any suitable desired kind, including, apart from the flat contacts shown which provide two line-shaped contact areas, preferably also two dot-shaped contact areas for accurate fixing of the point of contact. However, it is also possible to provide in each contact coating a minor recess which is adapted somewhat to the circumference of the syringe tube.

Instead of relatively soft contact coatings 108 made, for example, of Ag, it is also possible to provide hard coatings, e.g. of W. If desired, it is even possible to dispense with separate contact coatings and make the entire tongs, at least the area of the jaws thereof, of a preferably hard contact material.

The contact pressure is exerted by a light compression spring 110 closing the head of the tongs and having a very small contact pressure in comparison with the clamping force between the jaw member 64 and the piston rod 85.

For opening of the electrode tongs 100 a cam or wedge face 112 is formed at the rear end of each of tongs halves 106 and a respective cam pin 114, displaceable in opening direction of the tongs, may act on each cam face. The pivoting movement of the cam pins 114 required for opening the tongs is indicated by a double arrow 116 in FIG. 1. It is effected by limited pivoting of the cam pins 114 by means of an actuating shaft 118 which is moved back and forth in a fixed cycle.

Sometimes it is considered disadvantageous to have the opening and/or closing motions of the tongs take place with too much impact. In that event it is recommendable to control the opening and/or closing smoothly by means of a control curve, e.g. a guide bar, slot guidance, or cam.

Twice the clamping jaw 60 carries out a vertical working stroke. During the first phase it is moved upwardly along line 68 to introduce the syringe tube into the fitting in the position shown in FIG. 1 and, at the same time, pivoted into a position ready for insertion, as described above. The second phase takes place during the passage of the welding current through the contact coating 108 connected to the welding current generator, then through the section of the syringe tube extending through the fitting, and finally through the counterelectrode 98 which is likewise connected to the welding current generator. This second phase of the stroke is shown exaggerated by double arrow 120. Overcoming the clamping force, the clamping face of piston rod 84 as well as the clamping face on jaw member 64 slide by an undefined distance along the syringe tube supported by the counterelectrode 98 which is stationary with respect to the jaw member because, during the passage of current, at the same time a certain erosion takes place between the counterelectrode and the inner end 24 of the syringe tube 4. Yet this is balanced by the second phase of the upward movement of the clamping jaw. As the clamping jaw does not function to transmit current, the clamping and gliding faces entering into engagement with the syringe tube may be given their optimum design, e.g. may be made of suitable sliding material causing only little grooving, if desired, even of suitable metals or plastic material, such as polytetrafluoroethylene.

As also the electrode tongs is stationary, the free end 22 of the syringe tube 4 also must be able to slide with respect to the contact faces of the contact coating 108. The slide distance is determined by the erosion between the inner end 24 of the syringe tube and the counterelectrode. Because of the weak force of the compression spring 110 there is only little resistance to the sliding movement, a resistance which can be kept much smaller than the clamping force by which the syringe tube is gripped in the clamping jaw 60. On the other hand, there is always an exactly predetermined constant length of the syringe tube between the two electrodes during the entire passage of current between the counterelectrode 98 and the contact coating 108 so that the effective heating resistance during the fusing process remains constant, regardless of the length of the erosion loss at the inner end 24 of the syringe tube.

As the electrode tongs engages the syringe tube directly below its exit from the fitting 6 between the latter and the highest position of the stroke of the clamping jaw, the resistance path outside of the fitting is just a minimum so that the syringe tube practically can become discolored only in the area of the constriction 18 or somewhat below the same. Yet the constriction may be selected such that it will be closed by plastic material during the fusing procedure so that practically no useless annealing takes place in areas which lie between the injection tip 8 of the syringe tube 4 and the fitting 6. As it is this particular area which is subjected to great mechanical stress when using the hypodermic syringe, it can be protected much better than before from becoming brittle or soft, and also the discoloration otherwise caused by annealing can be avoided.

When the syringe tube has been fused in, the clamping jaw 60 may be opened again and returned into the lower starting position shown is chain lines in FIG. 1 so as to be ready for repeating the cycle. The current conductor 94 is withdrawn accordingly to such an extent that the counterelectrode 98 is moved out of the fitting. Then the finished disposable syringe 2 can be discharged and conveyed to another processing station by means of the carrier plate 26 which, for example, may be disposed on a great turntable.

In connection with FIG. 3, which shows parts broken away, reference was already made to multiplying the stations according to FIGS. 1 and 2, for example by showing several storage spaces 32 of the syringe tube magazine 30 and entries 46 which each lead to a glide rail 59 according to FIG. 1. In such a multiple, for example tenfold, arrangement, of course, there are also ten electrode tongs 100, cylinders 82, receiving apertures 28 etc.

Electrical resistance measurement may be provided between the clamping jaw 60 designed as a measuring electrode and individual, mutually insulated portions of the baffle plate 72 in order to detect whether or not a syringe tube has reached its operative position. In that case the friction roller 78 conveniently is made of material which is electrically non-conductive. As an alternative, the friction roller 78 could also be selected to be the measuring counterelectrode. This will permit inquiry to find out in which measuring paths there is electrical resistance. Then the overall welding capacity required for all fusing positions can be adjusted accordingly.

Figure 4:
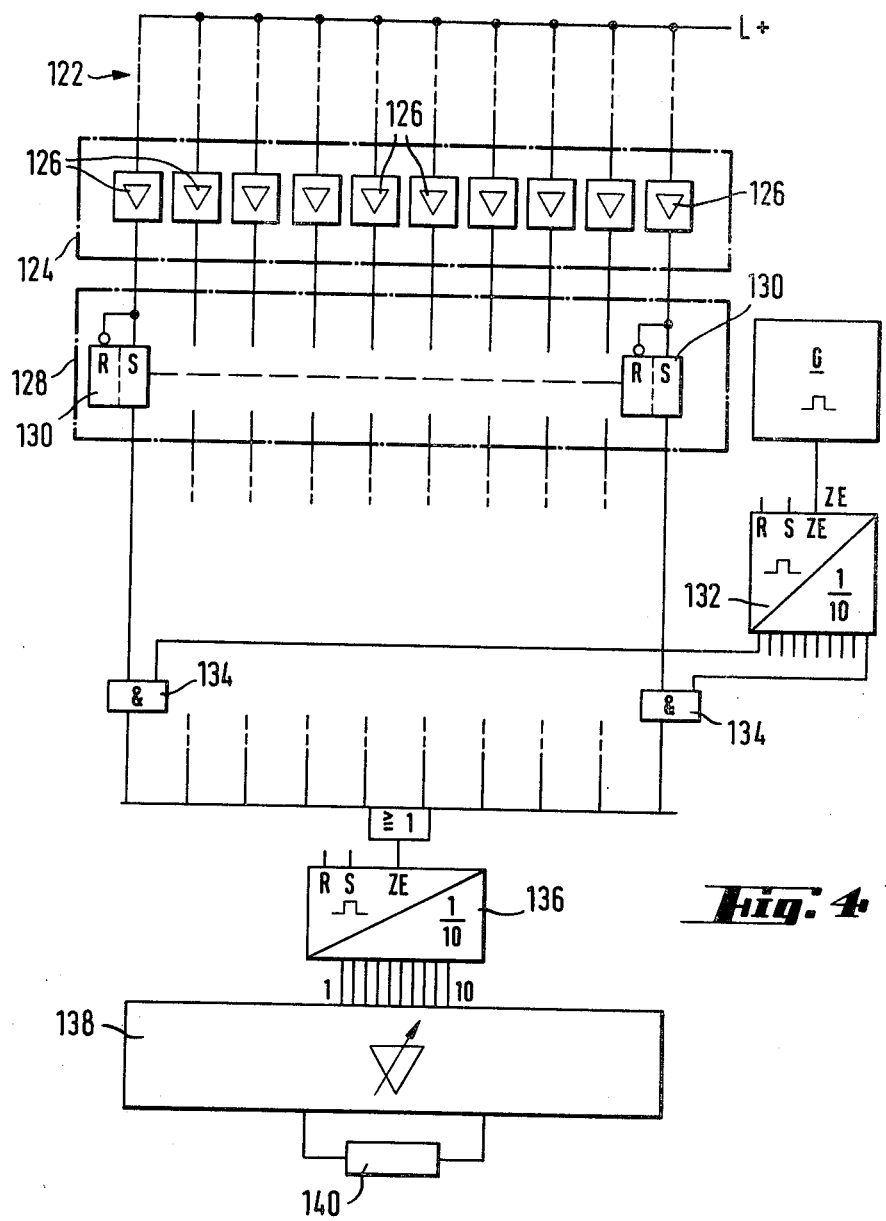
FIG. 4 is a circuit diagram of an electrical means to be used in connection with the apparatus according to FIGS. 1 to 3 for adjusting the fusing performance in response to the number of syringe tubes made available for fusing at different operating positions of a multiple means.

A corresponding electrical circuit of the welding voltage generator connected on the one hand with the current carrying part of the electrode tongs 100 and on the other hand with the counterelectrode 98 is shown in FIG. 4.

FIG. 4 is an example of a multiple arrangement including ten control positions 122. In general, an indefinite number "n" of such control positions can be provided in correspondence with the number of syringe tubes to be fused at the same time in corresponding fittings.

The control positions are located between the clamping jaw 60 and the individual contact positions on the baffle plate 72 which are insulated with respect to one another.

When applying a voltage between pole L+ which, for example, is positive and a counterpole on an amplifier means 124, current passes through all syringe tubes which are in clamped position. The signals given during the passage of current are amplified in an amplifier 126 each, associated with each resistance measuring path, so that they can each set an R-S-flip-flop in a control memory 128. Where no current passage occurs, the flip-flop is not moved out of its basic position. In a single measuring step thus the actual picture as to where there the syringe tubes can be imaged in the control memory 128 in each individual flip-flop 130.

Furthermore, a clock generator G is provided, by the clock pulses of which an interrogation counter 132 is incremented in steps so that at its ten outputs interrogation pulses are provided successively. These are linked by means of individual AND circuits 134 with the output signals of the corresponding flip-flop 130 of the control memory 128 and registered in a control counter 136. A capacity adjustment unit 138 is so adjusted in response to the count registered that the welding apparatus 140 always provides a welding capacity adapted to the respective number of syringe tubes located in operative position. Thus it is possible to obtain a predetermined welding capacity for each syringe tube, regardless of whether or not syringe tubes are available at the other operating stations.

The close contact required for resistance welding between the syringe tube 4 and the fitting 6 conveniently is obtained in the manner shown in the form of various modifications in FIGS. 5 to 9.

Figure 5:
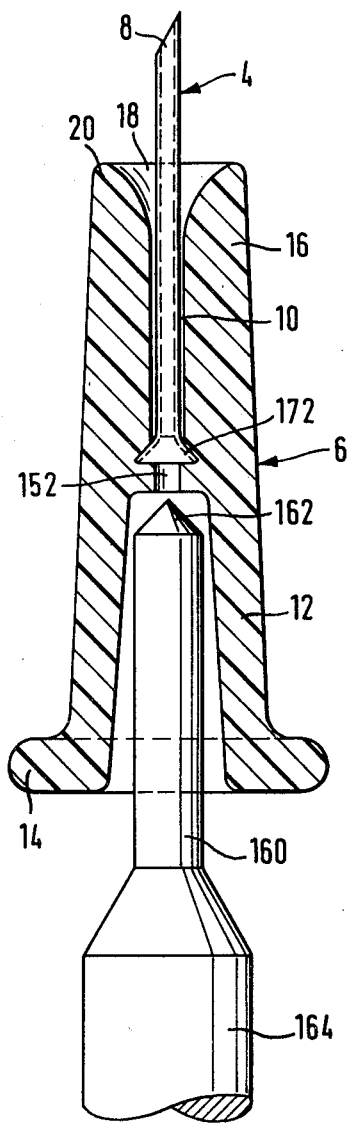
FIG. 5 is an axial cross-sectional elevational view of the syringe tube and its fitting in unconnected condition, including a flaring expander.
Figure 6:
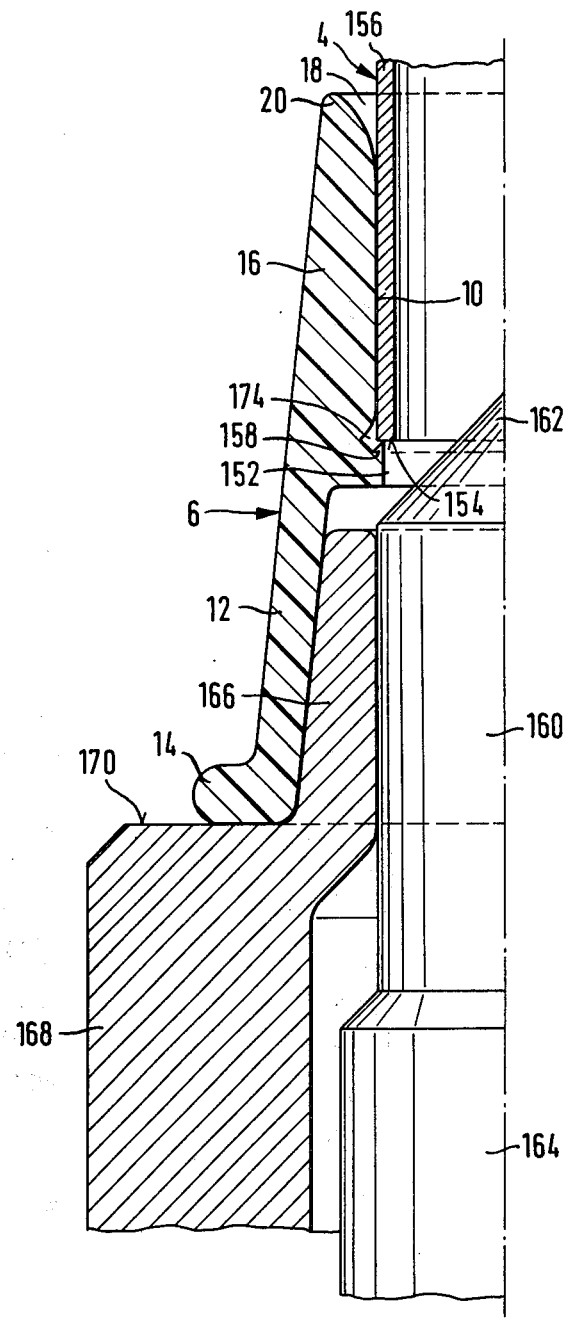
FIG. 6 is an axial cross-sectional view of an alternative embodiment of FIG. 5, including a holder for the fitting.

According to FIGS. 5 and 6 the fitting 6 has the same outer configuration as shown in FIG. 1. The same applies to FIGS. 7 and 9a and 9b which, however, do not include the cup- or pot-shaped portion 12 and with which the base 16 may be connected directly, for instance, by welding its front end connecting face 150 directly to the cylinder of a hypodermic syringe. The peculiarities of FIGS. 5 to 9b reside in the internal configuration of the central bore provided in the base 16, the selected shape of the syringe tube 4, and the possible outer configurations of the fitting prior to the final connection with the syringe tube according to FIGS. 9a and 9b.

The peculiarities provided according to FIGS. 5 and 6 can be transferred mutatis mutandis to FIGS. 7, 9a and 9b and vice versa. The alternatives according to FIGS. 8a and 8b likewise are useful also with an embodiment of the fitting 6 as shown in FIGS. 5 and 6 as well as with the shapes of the fitting shown in FIGS. 7, 9a and 9b.

All embodiments according to FIGS. 5 to 9 start from the fact that first the syringe tube 4 is inserted loosely into the central bore 10 and is subsequently expanded to create a tight embrace by the base 16 of the fitting 6.

In contrast to the arrangement shown in FIG. 1, the syringe tube 4 does not extend all the way into the free space of the cup-shaped portion 12. Instead it ends before a constriction 152 of the central bore 10 at the transition into the pot- or cup-shaped portion 12 according to FIG. 5 or FIG. 6 or at the connecting face 150 for a hypodermic syringe according to FIG. 7 or FIG. 9. It is most advantageous to provide the arrangement of FIG. 6 with which the relationship between the inner width of the syringe tube 4 and the inner width of the constriction 152 and the remainder of the bore 10 in the base 16 is so selected that according to FIG. 6 a front end face 154 of a wall 156 of the syringe tube 4 is seated only with its outer end annular face on an annular step 158 of the constriction 152 in the bore 10. The inner end annular face of the wall 156 of the syringe tube, on the other hand, is disposed opposite the inner opening of the constriction 152. This requires very close tolerances of the cooperating members because the usual wall thicknesses of a syringe tube are about 1.0 or 1.5 mm with outer diameters of the syringe tubes between 0.6 mm (and less) and 2.0 mm (and more). 2.0 mm and 0.6 mm are the upper and lower limits, respectively, of the syringes most commonly used, and the actual dimensions rather tend to lie in the central range between the limits indicated.

As rather hinted at in FIG. 5, according to an alternative the inner width of the syringe tube may be so selected that from the very beginning it is not smaller than the inner width of the constriction 152 and the constriction may be deformed more strongly than the syringe tube, provided that the constriction is of sufficient elasticity and adjusting force.

Contrary to FIG. 1, in other words in accordance with the embodiments shown in FIGS. 5 to 9, the inner end of the syringe tube 4 ends within the base 16 rather than projecting into the free space at the backside of the base, as shown in FIG. 1 in order to facilitate the flush engagement with the counterelectrode 98.

The syringe tube 4 which at first is supported on the constriction 152 then is fixed mechanically in the fitting by being expanded. A flaring expander or mandrel 160 conveniently provided with a conical tip 162 is used for expanding. The effective part of the mandrel 160 conveniently is so dimensioned that it either fits exactly through the inner width of the constriction 152 (FIG. 6) or is a little wider or perhaps even much wider in cross-section (FIG. 5) than the inner width of the constriction 152. In the case of surplus width with respect to the inner width of the constriction 152 the expanding process starts from the assumption that the plastic material of the constriction is so resilient that the mandrel 160 serves not only to expand the syringe tube but can also displace the plastic material of the constriction 152 in the base 16 of the fitting 6. Then more or less elasticity can be provided to return the plastic material into its initial condition when the expanding of the syringe tube is finished.

The mandrel 160 used for expanding is fixed to or made integral with a shaft 164 which remains outside of the fitting 6 even during the expanding stroke. The shaft 164 is connected to a conventional indexing disc. The mandrel 160 is so dimensioned that it fits with considerable clearance into the inner free space of the cup-shaped portion 12 in the case of fittings 6 having a cup-shaped portion 12, as shown in FIG. 5 or FIG. 6. According to FIG. 6 a holding stud 166 of a holding member 168 of an assembly machine may extend into this free space. The holding member 168 may be a component part of an index plate. As shown in FIG. 6, the arrangement may be such that the outside face of the holding stud 166 cooperates essentially in form lock with the inside face of the cup-shaped portion 12 and, if desired, the cup-shaped portion 12 additionally or alternatively rests by its flange-like enlargement 14 on a front end face 170 of the holding member 168 facing the same. The inner bore in the holding stud 166 at the same time may serve as a guide means for the mandrel 160 used for expanding.

It is possible to provide only one expansion of a relatively short portion at the inner end of the syringe tube 4, using for this expanding process only the tip 162 of the mandrel 160. This will result in a trumpet- or bell-shaped expansion 172 as shown in FIG. 5. This expansion either may be achieved by displacing material of the wall of the central bore 10 in the base 16 or into a preformed enlargement 174 in the central bore complementary to the shape of the expansion, as shown in FIG. 6.

FIG. 6 shows the syringe tube 4 before being expanded, while FIG. 7 shows it in expanded condition with a preformed enlargement 174 of the bore 10, and FIG. 5 shows a syringe tube which has been expanded against elastic deformation.

Although, for reasons of simplicity, FIG. 5 does not show a deformation of the outline of the fitting 6 corresponding to the elastic deformation, such deformation of the outer configuration may occur by the displacement of material. FIG. 9 shows a measure to partly or fully compensate that by providing, as in FIG. 9a, an inclination 176 or, according to FIG. 9b, a waistline 178 in the prefabricated form of the fitting 6 at the location where material of the fitting will be displaced when expanding the syringe tube. Under ideal conditions this will provide the expanded finished configuration shown in FIG. 5 with which no displacement of material towards the outside can be recognized along the outline of the fitting. Of course, the shape of the outer recess provided in the prefabricated fitting depends on the selected deformation of the syringe tube and on the position of this deformation along the fitting as well as on the characteristics of the plastic material of which the fitting is made.

Instead of forming an essentially conical expansion at the inner end of the syringe tube 4, FIGS. 9a and 9b show the extreme case in which a cylindrical expansion is obtained along the entire length of engagement of the central bore 10 between the constriction 152 and the exit from the fitting. A very advantageous compromise between a cylindrical expansion and an expansion at the inner end of the syringe tube only is shown in FIG. 8a according to which the syringe tube is expanded not only by means of the tip 162 of the mandrel 160 but also partly by the shaft 164 thereof so that an initial cylindrical section 180 is formed accordingly at its inner end and this section merges into a conical transitory section 182 and finally into a section of the syringe tube 4 which is not expanded.

In the case of the arrangement shown in FIGS. 9a and 9b, the syringe tube 4 is supported against pressure in the direction of the hypodermic syringe by form lock in that it is supported on the shoulder of the construction 152 in the central bore 10, whereas the support against tension is obtained only by friction lock. With the other embodiments, support in form lock is established in both directions because also the resistance against tension is guaranteed by form lock of the syringe tube in the base 16 of the fitting 6.

As an alternative to the technique of expanding shown, other known expansion methods can be applied, such as the method known in connection with the production of cartridges for ball point pens with which a pleat 184 or other corrugation is formed in the area of the syringe tube disposed within the base 16. With this arrangement the constriction 152 may be dispensed with.

If the shaft 164 is given appropriate shape, the flaring expander 160 may also take over the function of the counterelectrode 98 according to FIG. 1.

If the syringe tube is mounted so as to resist a tensile force of at least 6 kp, this is sufficient for pre-fixing the syringe tube 4 in the fitting 6. However, a somewhat greater resistance against tensile forces is more advantageous. In the extreme case, values of tensile strength of 6 kp, 8 kp or considerably more can be reached. This will make it possible to obtain a corresponding assembly of a metal syringe tube and plastic fitting, which assembly is sufficiently resistant against pressure and tension and sufficiently tightly sealed, if desired, even without any subsequent welding or fusing.

Yet it is a condition that the work is done carefully and close tolerances are observed. In general, it will be sufficient to expand the outer diameter of the syringe tube by about 1/10 mm, and in some cases even less. Preferably, the expansion is made by at least several tenths of a millimeter, conveniently more than 20% of the outer diameter of the syringe tube. The material of the fitting, for instance including a polycarbonate, must be compatible with such expansion if it is displaced during the expanding procedure.

It is convenient to introduce the flaring expander or mandrel under vibration into the syringe tube when expanding the same. The vibration of the mandrel may be caused in axial or in circumferential direction. It is also possible to provide for axial vibration of a rotating mandrel. Convenient for use in this context are low frequency vibrations at a frequency from 10 Hz on.

In respect of the embodiments of the fitting 6 according to FIGS. 5 to 9b, the constriction 152 of the bore 10 can be expanded more or less by the mandrel 160 during expanding the syringe tube 4, and then it depends on the resetting power and on the quality of the elasticity of the displaced material of the constriction 152 to what extent said constriction 152 adjusts again to the original configuration after withdrawing the mandrel 160 and resumes its function as support of the syringe tube 4 against pressure and, possibly, as means for sealing the syringe tube in respect of the fitting.

This difficulty can be avoided by manufacturing the bore 10 firstly without constriction 152, e.g. as a bore having a cross-sectional area which is constant over the length of said bore, or by manufacturing the bore with a constriction 152 which is so amply dimensioned that it is not expanded by the mandrel itself. In such cases, it is possible to improve the supporting and sealing function of the constriction 152 in the following manner:

Firstly, a portion of the syringe tube 4, which is inserted into the bore 10 to such an extent that the desired position of installation is reached, is expanded, and, thus, the syringe tube is retained in the fitting 6, firstly at least against tensile load. Then, wall material of the bore 10 in the fitting 6 is heated until a deformable, and possibly fluid, state is reached and shifted in front of the inner end of the syringe tube 4 for the purpose of forming only then a constriction 152 supporting the syringe tube against pressure or for the purpose of reinforcing a constriction which has already been provided and, respectively, for the purpose of providing such a constriction with a smaller inner cross-sectional area. The displaced wall material may also be used for adhering the syringe tube 4 in the fitting 6.

It is mostly necessary to keep the inner surface of the syringe tube free from plastic material and, furthermore, it is also necessary to leave free an inner flow channel in the bore 10 of the fitting 6 behind the rear end of the syringe tube. A separate sealing mandrel may be used for this purpose, which can be sealingly introduced into the inner end of the syringe tube 4 after the syringe tube 4 has been expanded. For the purpose of heating the plastic material of the fitting 6 in the wall region of the bore 10 behind the inner end of the syringe tube 4, a hollow heating piston may be used which is preferably heat-insulated and which may be guided on the sealing mandrel. This heating piston displaces the plastic material after the inner end of the syringe tube 4 has been sealed and after the plastic material to be displaced has been sufficiently heated.

It is expedient in the case described to perform the expansion of the syringe tube 4 at a first working station and the displacement of the plastic material at a second working station in order to obtain fast cycles.

However, it is also possible to use the expanding mandrel 160 at the same time as a sealing mandrel and, eventually, to guide the heating piston. In this case it is expedient to perform expansion and plastics displacement at the same working station.

The sealing mandrel, or, respectively, the expanding mandrel 160, may remain in engagement with the inner end of the syringe tube 4 until the displaced plastics material has sufficiently solidified.

The heating piston and the sealing mandrel or the expanding mandrel may form a single tool in the case of which the sealing mandrel or expanding mandrel becomes active before the heating piston.

FIGS. 10 to 15 show an apparatus in which an expansion and subsequent formation of plastic material of the fitting in front of the syringe tube is performed by means of two successive tools 200 and 204, conveniently at two successive working stations, whereas FIGS. 16 to 18 show an alternative thereto, in which only one tool 220 is used, conveniently at the same working station.

In respect of the first alternative, the fitting 6 is provided with a continuous bore 10 which may have a cross-sectional area which is constant over the total length thereof. In this case, the positioning of the syringe tube 4 in its mounting position in the fitting can be ensured be external supporting means. However, it is also possible, as shown in the instant case, to provide a small step 10a in the bore for the purpose of defining the final position.

For the purpose of expanding the syringe tube, an expanding mandrel 200, the outer diameter of which corresponds at least approximately to the inner diameter of the bore 10 behind the final position of the inner end of the syringe tube 4 (and which fits into the bore section 10b), is axially displaced in the direction of the arrow fron the initial position of FIG. 10 (after introducing the syringe tube 4 in the direction of the arrow against the step 10a) to the expanding position according to FIG. 11, until the inner end 201 of the syringe tube 4 has expanded in a trumpet-like manner, either against the material of the fitting or in a recess provided therein. Then, said mandrel 200 is retracted to an initial position in which it is not in engagement, as shown in FIG. 12.

The second tool 204 according to FIG. 13 is positioned in the next working station. Said tool 204 comprises a sealing projection 205 and a heating ring 206. The object is to fill the zone 202 with plastic material which is in the preshaped configuration of the fitting 6 in the zone 203. For this, the sealing projection 205 is firstly sealingly introduced into the inner end of the syringe tube 4 in accordance with FIG. 14. Although the sealing projection 205 can be formed in this case integrally with the heating means resembling a heating piston, the sealing pin 205 can also be axially guided within a separately produced heating piston. As soon as the heating means has reached the position according to FIG. 14, the plastic material is displaced in the direction of the arrows 207 from the fitting to the final position. It can be seen that the sealing mandrel 205 is also a calibrating mandrel for the continuation of the inner channel of the syringe tube.

FIG. 15 shows the final position in which tool 204 is no longer in action.

In respect of the alternative construction according to FIGS. 16 to 18, the sole tool 220 comprises an expanding mandrel 210 located axially inside a sliding sleeve 211 surrounding said mandrel 210 and consisting possibly of thermally insulating material, as well as a hollow heating piston 212 which, in turn, is axially guided on said sliding sleeve 211.

According to FIG. 16 the syringe tube 4 is expanded in the manner described hereinbefore in a first work phase by means of the unit 210, 211, the combination of which serves as expanding mandrel.

In the next work phase according to FIG. 17, the inner part of the expanding mandrel 210 is further introduced into the syringe tube to a sealing position, while the sleeve 211 is somewhat axially retracted substantially at the same time. Thus, a space 202 is formed between the expanded inner end of the syringe tube 4 and the opposite end of the sleeve 211, which space 202 is adapted to communicate with an inner venting channel (not shown) within the piston-like mandrel 210 through openings (not shown). However, it is also possible to provide other vents, e.g. longitudinal channels in the guiding means between the sleeve 211 and the mandrel 210.

The third work phase includes an extrusion-like process with simultaneous thermal cooperation of the heated heating piston 212. In this process material is again formed in accordance with the arrow 207 in front of the end of the syringe tube 4.

The expanding mandrel preferably has a circular cross-sectional area and a cone-shaped or inwardly flared pointed tip.

What we claim is:

1. In a method for fusing a metallic syringe tube having an inner end and a free end into a plastic fitting by pushing the inner end of the syringe tube into the fitting so that the inner end of the syringe tube contacts the fitting, clamping the syringe tube between a counterelectrode which acts as an abutment for the inner end of the syringe tube and a clamping jaw which engages the free end of the syringe tube, and temporarily applying a resistance heating voltage between the counterelectrode and the free end of the syringe tube projecting from the fitting for heating at least a portion of the syringe tube inner end in contact with the fitting to at least the melting temperature of the plastic forming the fitting, while at the same time displacing the clamping jaw and the counterelectrode relatively toward one another, the improvement wherein said step of applying a resistance heating voltage is carried out by applying such voltage between the counterelectrode and a location on the free end of the syringe tube between the fitting and the clamping jaw such that the voltage is applied along a length of the syringe tube which is shorter than the length of the syringe tube between the clamping jaw and the counterelectrode, and said method further comprises maintaining the length of the syringe tube along which the voltage is applied substantially constant during said step of temporarily applying.

2. The method as claimed in claim 1, wherein the clamping jaw is displaced in the direction towards the fitting during the application of the resistance heating voltage, and the resistance heating voltage is applied to the free end of the syringe tube at an unvarying spacing from the fitting.

3. The method as claimed in claim 1 or 2 wherein a plurality of syringe tubes are fused simultaneously into a respective plurality of plastic fittings, and are subjected to a common resistance heating voltage, further comprising counting the number of syringe tubes gripped by the clamping jaw and adjusting the fusing conditions in accordance with the counting result.

4. The method as claimed in claim 1 or 2 wherein the syringe tubes are placed in a magazine and singled out by a separating slide means, and further comprising applying to each tube a withdrawal force which acts as a friction force on each syringe tube disposed in the separating slide means.

5. The method as claimed in claim 1 or 2, further comprising, before clamping the free end of the tube in the clamping jaw, fixing the syringe tube in a selected position relative to the clamping jaw by an auxiliary force.

6. The method as claimed in claim 5, wherein the syringe tube is thrown against a baffle face when being introduced into the clamping jaw, further comprising holding the syringe tube in abutment against the baffle face by a return force until the clamping jaw comes to clamp the tube.

7. The method as claimed in claim 5, wherein the syringe tube is brought into engagement with a surface having a selected position relative to the clamping jaw by an entrainment force which aligns the syringe tube in the open clamping jaw.

8. The method as claimed in claim 1 further comprising expanding a section of the syringe tube extending within the fitting for securing the tube to the fitting.

9. The method as claimed in claim 8 wherein said step of expanding is carried out by inserting into the syringe tube inner end an expansion mandrel also constituting the counterelectrode.

10. The method as claimed in claim 8 wherein said step of expanding is carried out by inserting into the syringe tube inner end an expansion mandrel.

11. The method as claimed in claim 10 wherein said step of inserting comprises rotating the mandrel.

12. The method as claimed in claim 10 wherein said step of inserting comprises vibrating the mandrel.

13. The method as claimed in claim 8 wherein a tension-proof and compression-resistant engagement is established by said step of expanding.

14. The method as claimed in claim 13 wherein the fitting is initially provided with a recess adjacent the inner end of the syringe and further comprising, during said step of expanding, filling the recess with material of the fitting.

15. The method as claimed in claim 13 wherein the fitting is provided with a preformed recess into which the tube is expanded during said step of expanding.

16. The method as claimed in claim 13, wherein the counterelectrode is applied to the inner surface of the syringe tube.

17. The method as claimed in claim 13 wherein a tension resistance of more than 3 kp is produced.

18. The method as claimed in claim 17 wherein the tension resistance is more than 8 kp.

19. The method as claimed in claim 13 further comprising, prior to said step of expanding, supporting the syringe tube on the shoulder of a constriction of an axial bore extending through the fitting, and wherein said step of expanding is carried out by passing a mandrel through the constriction.

20. The method as claimed in claim 19, wherein said step of supporting is carried out by supporting the syringe tube on the shoulder of the constriction by the outer zone of its wall thickness only.

21. The method as claimed in claim 1 further comprising, during said step of applying a resistance heating voltage, displacing the clamping jaw and the counterelectrode relatively towards each other.

22. A method of producing a disposable syringe component composed of a syringe tube of metal and a fitting of a softenable or meltable material having a central bore, comprising inserting the syringe tube into the bore so that the syringe tube projects out of the fitting, expanding the syringe tube within the bore, and subsequent to expanding the syringe tube, deforming a portion of the fitting material by softening or melting that portion and displacing that portion to a position in front of the inner end of the syringe tube to form a constriction opposite the inner end of the syringe tube, such that in both axial directions of the syringe tube, material of the fitting is located opposite the expanded portion and the tube is connected to the fitting in a sealed, compression- and tension-resistant manner.

23. The method as claimed in claim 22 comprising, prior to the deformation of the material, sealing the inner end of the syringe tube against access of plastic material.

24. In a method for fusing a metallic syringe tube having an inner end and a free end into a plastic fitting by pushing the inner end of the syringe tube into the fitting, clamping the syringe tube between a counterelectrode which acts as an abutment for the inner end of the syringe tube and a clamping jaw which engages the free end of the syringe tube, and temporarily applying a resistance heating voltage between the counterelectrode and the free end of the syringe tube projecting from the fitting, the improvement comprising supporting the syringe tube on the shoulder of a constriction of an axial bore extending through the fitting, and, after said step of supporting, laterally expanding the inner end of the syringe tube within the fitting by passing a mandrel through the constriction for securing the tube to, and establishing a tension-proof and compression-resistant engagement with, the fitting.

25. The method as claimed in claim 24 wherein said step of supporting is carried out by supporting the syringe tube on the shoulder of the constriction by the outer zone of its wall thickness only.

26. In a method for fusing a metallic syringe tube having an inner end and a free end into a plastic fitting by pushing the inner end of the syringe tube into the fitting, clamping the syringe tube between a counterelectrode which acts as an abutment for the inner end of the syringe tube and a clamping jaw which engages the free end of the syringe tube, and temporarily applying a resistance heating voltage between the counterelectrode and the free end of the syringe tube projecting from the fitting, the improvement wherein the fitting is initially provided with a recess adjacent the inner end of the syringe tube, and comprising laterally expanding the inner end of the syringe tube within the fitting for securing the tube to, and establishing a tension-proof and compression-resistant engagement with, the fitting, and, during said step of expanding, filling the recess with material of the fitting.

27. In a method for fusing a metallic syringe tube having an inner end and a free end into a plastic fitting by pushing the inner end of the syringe tube into the fitting, clamping the syringe tube between a counterelectrode which acts as an abutment for the inner end of the syringe tube and a clamping jaw which engages the free end of the syringe tube, and temporarily applying a resistance heating voltage between the counterelectrode and the free end of the syringe tube projecting from the fitting, the improvement comprising laterally expanding the inner end of the syringe tube within the fitting, by inserting into the syringe tube inner end an expansion mandrel also constituting the counterelectrode, for securing the tube to the fitting.

28. In a method for fusing a metallic syringe tube having an inner end and a free end into a plastic fitting by pushing the inner end of the syringe tube into the fitting, clamping the syringe tube between a counterelectrode which acts as an abutment for the inner end of the syringe tube and a clamping jaw which engages the free end of the syringe tube, and temporarily applying a resistance heating voltage between the counterelectrode and the free end of the syringe tube projecting from the fitting, the improvement comprising laterally expanding the inner end of the syringe tube within the fitting by inserting an expansion mandrel into the syringe tube inner end for securing the tube to the fitting, wherein said step of inserting comprises rotating the mandrel.

29. In a method for fusing a metallic syringe tube having an inner end and a free end into a plastic fitting by pushing the inner end of the syringe tube into the fitting, clamping the syringe tube between a counterelectrode which acts as an abutment for the inner end of the syringe tube and a clamping jaw which engages the free end of the syringe tube, and temporarily applying a resistance heating voltage between the counterelectrode and the free end of the syringe tube projecting from the fitting, the improvement comprising laterally expanding the inner end of the syringe tube within the fitting by inserting an expansion mandrel into the syringe tube inner end for securing the tube to the fitting, wherein said step of inserting comprises vibrating the mandrel.

* * * * *